March 22, 1955 H. C. SWIM Plant Pat. 1,368
ROSE PLANT
Filed June 14, 1954
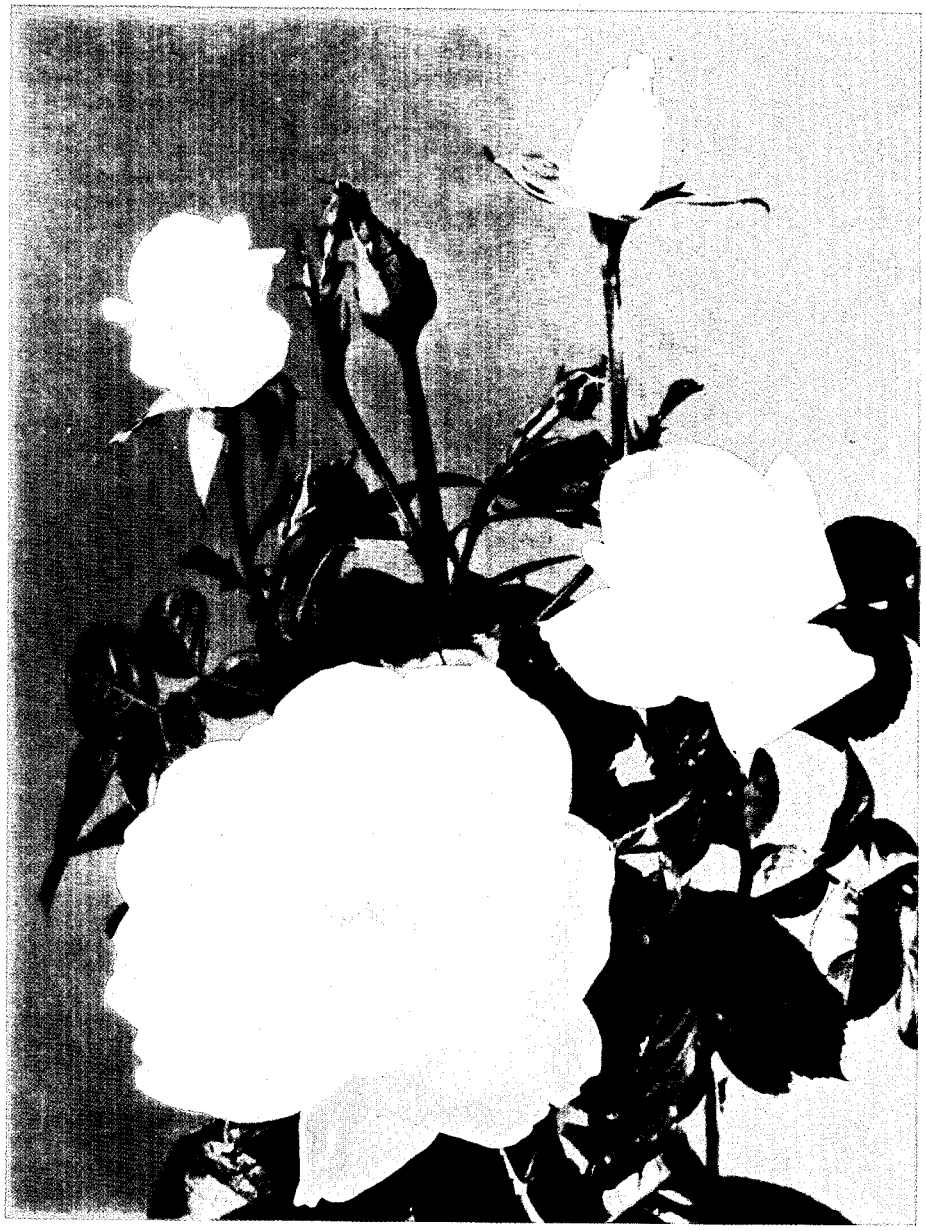
Inventor.
H. C. Swim
By: Robb & Robb
Attorneys.

United States Patent Office

Plant Pat. 1,368
Patented Mar. 22, 1955

1,368

ROSE PLANT

Herbert C. Swim, Ontario, Calif., assignor to Armstrong Nurseries, Inc., Ontario, Calif., a corporation of California Application June 14, 1954, Serial No. 436,752

1 Claim. (Cl. 47—61)

The present invention relates to a new and distinct variety of rose plant of the hybrid polyantha class, which was originated by me by crossing the variety "Fandango" (Plant Patent No. 894) with the variety "Pinocchio" (Plant Patent No. 484).

The primary objective in making the aforementioned cross was to produce a new rose variety which combines the most desirable characteristics of the two parent varieties, and thereby resulting in definite improvements over the parent varieties, as well as over all others of the same class. This objective was fully achieved, as evidenced by the fact that my new variety produces blooms of a size approaching those of the seed parent "Fandango," the blooms are usually borne in clusters similar to the habit of the pollen parent "Pinocchio," the blooms have a distinctive Yellow general color tonality derived from the recessive genes contributed by both parent varieties, and the foliage of the new variety is produced in an abundance corresponding to that of the parent "Fandango" and covers the plant very well.

As compared with its parent variety, "Fandango," the blooms of my new variety are a light shade of yellow, whereas those of this parent are a medium shade of red, which is popularly described as "cherry red"; the blooms of the new variety are frequently and usually produced in clusters of several per stem, whereas those of this parent are usually produced singly and only occasionally with two or three per stem; and the blooms of the new variety are double in petalage, having from 35 to 45 petals, whereas those of this parent are semi-double and have only from 16 to 25 petals.

In comparison with its parent variety, "Pinocchio," the light yellow blooms of my new variety are distinctly different from those of this parent which bears blooms that are popularly described as pink-suffused salmon color; the blooms of the new variety are larger in size than those of "Pinocchio," measuring from 3½ inches to 4½ inches in diameter, whereas those of this parent measure only about 2 inches in diameter; and the foliage of my new variety is more abundant and of larger size than that of "Pinocchio," and covers the plant much better.

Asexual reproduction of my new variety by budding, as performed at Ontario, California, shows that the foregoing characteristics and distinctions come true to form and are established and transmitted through succeeding propagations.

The accompanying drawing shows typical specimens of the flowers and foliage of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (herein abbreviated as "Wilson") and Robert Ridgway's Color Standards and Nomenclature (herein abbreviated as "Ridgway"), as indicated:

Type: Bush; outdoor; seedling; for cut flowers and for garden decoration.
Class: Hybrid polyantha.
Breeding: Seedling.
*Seed parent.*—"Fandango."
*Pollen parent.*—"Pinocchio."
Propagation: Holds its distinguishing characteristics through succeeding propagations by budding.

FLOWER

Locality where grown and observed: Ontario, California.
Flowers borne: Usually 4 or 5 or more to stem; in regular, rounded clusters; on strong, long stems.
Quantity of bloom: Abundant, outdoors.
Continuity: Continuous during growing season.
Fragrance: Penetrating. Nature—Tea to spicy.
Bud:
*Peduncle.*—Average length; average caliper to heavy; erect; usually smooth; some gland-tipped cilia; few prickles. Color—Near Absinthe Green, Plate XXXI (Ridgway), overlaid with near Deep Corinthian Red, Plate XXVII (Ridgway) on side exposed to the sun.
*Before calyx breaks.*—Size—medium. Form—medium length; ovoid; with foliaceous appendages; with few gland-tipped cilia on the surface of the bud; usually without much-cut foliaceous parts extending beyond the tip of the bud.
*As calyx breaks.*—Color—near Lemon Yellow, Plate 4/3, page 4 (Wilson).
*Sepals.*—Inner surface with fine woolly tomentum; margins of alternate sepals lined with fine woolly tomentum; others lined with gland-tipped cilia.
*As first petal opens.*—Size—average to large. Form—medium length to long; urn-shaped.
Color: Outside—between Aureolin, Plate 3/3, page 3 (Wilson) and Lemon Yellow, Plate 4/3, page 4 (Wilson); small area at base of petal near attachment near Aureolin, Plate 3/2, page 3 (Wilson). Inside—between Aureolin, Plate 3/3, page 3 (Wilson) and Aureolin, Plate 3/2, page 3 (Wilson); small area at base of petal near attachment near Aureolin, Plate 3/1, page 3 (Wilson).
*Opening.*—Opens up well; is not retarded from opening by cold, hot, wet or dry weather.
Bloom:
*Size (when fully open).*—Very large for its class; from 3½ inches to 4½ inches.
*Petalage.*—Double; from 35 to 45 petals, plus 6 to 14 petaloids; arranged regularly.
*Form.*—High-centered at first, but becoming open to cupped later; petals at first being cupped, with lateral margins reflexed for approximately ⅓ of petal length, and lateral margins of outer petals reflexed ½ or more of petal length, with apex sometimes reflexed ¼ of petal length; becoming later, at maturity, flat-cupped, with lateral margins reflexed ¼ to ½ of petal length, and lateral margins of outer petals reflexed ¾ or more of petal length, and with apex sometimes reflexed ½ of petal length.
Petals:
*Texture.*—Medium to thick; moderately leathery; with inside satiny and outside from shiny to satiny.
*Shape.*—Outside—broadly obovate, with apex flat; rarely with 1 or 2 notches. Intermediate—Obovate, with apex rounded to flat; rarely with 1 or 2 notches. Inside—Narrowly obovate, with apex rounded; sometimes with 1 or 2 notches.

This description of a newly opened flower was made from a rose grown outdoors in the month of October, at Ontario, California:

Color:
*Outside petal.*—Outside surface—between Aureolin, Plate 3/3, page 3 (Wilson) and Empire Yellow, Plate 603/3, page 66 (Wilson); small area at base of petal near attachment near Aureolin, Plate 3/2, page 3 (Wilson). Inside surface—between Aureolin, Plate 3/3, page 3 (Wilson) and Empire Yellow, Plate 603/2, page 66 (Wilson); small area at base of petal near attachment near Aureolin, Plate 3/1, page 3 (Wilson).
*Intermediate petal.*—Outside surface—between Aureolin, Plate 3/3, page 3 (Wilson) and Empire Yellow, Plate 603/2, page 66 (Wilson); small area at base of petal near attachment near Aureolin, Plate 3/1, page 3 (Wilson). Inside surface—between Aureolin, Plate 3/3, page 3 (Wilson) and Empire Yellow, Plate 603/1, page 66 (Wilson); small area at base of petal near attachment near Aureolin, Plate 3/1, page 3 (Wilson).

*Inner petal.*—Outside surface—between Aureolin, Plate 3/2, page 3 (Wilson) and Empire Yellow, Plate 603/1, page 66 (Wilson); small area at base of petal near attachment near Aureolin, Plate 3/1, page 3 (Wilson). Inside surface—between Aureolin, Plate 3/2, page 3 (Wilson) and Empire Yellow, Plate 603/1, page 66 (Wilson); small area at base of petal near attachment near Aureolin, Plate 3/1, page 3 (Wilson).

This description was made from a rose that was open for 3 days outdoors in the month of November, at Ontario, California:

Color:

*Outside petal.*—Outside surface—from near Empire Yellow, plate 603/3, page 66 (Wilson) to near White near margins; small area at base of petal near attachment near Aureolin, Plate 3/3, page 3 (Wilson). Inside surface—from near Empire Yellow, Plate 603/3, page 66 (Wilson) to near White near margins; small area at base of petal near attachment near Aureolin, Plate 3/3, page 3 (Wilson).

*Inside petal.*—Outside surface—from near Empire Yellow, Plate 603/3, page 66 (Wilson) to near White near margins; small area at base of petal near attachment near Aureolin, Plate 3/3, page 3 (Wilson). Inside surface—near Empire Yellow, Plate 603/3, page 66 (Wilson); small area at base of petal near attachment near Aureolin, Plate 3/3, page 3 (Wilson).

General color effect:

*Newly opened flower.*—Between Aureolin, Plate 3/2, page 3 (Wilson) and Empire Yellow, Plate 603/1, page 66 (Wilson); small area at base of petals near attachment near Aureolin, Plate 3/1, page 3 (Wilson).

*3-days open.*—Between Empire Yellow, Plate 603/3, page 66 (Wilson) and Empire Yellow, Plate 603/2, page 66 (Wilson); small area at base of petals near attachment near Aureolin, Plate 3/3, page 3 (Wilson).

Behavior: Drop off cleanly; not particularly affected by cold, hot, wet or dry weather.

Flower longevity:

*On bush in garden.*—3 or 4 days in November.

*Cut roses grown outdoors and kept at living-room temperatures.*—3 or 4 days in November.

REPRODUCTIVE ORGANS

Stamens: Average number to many; arranged regularly about pistils.

Filaments: Medium length to long; from 6 to 12 mm. in length; most with anthers.

*Color.*—Between Buttercup Yellow, Plate 5/2, page 5 (Wilson) and Indian Yellow, Plate 6/2, page 6 (Wilson).

Anthers: Medium size; all open approximately at once.

*Color.*—Upper side—margins near Saffron Yellow, Plate 7/1, page 7 (Wilson), with remainder near Aureolin, Plate 3/3, page 3 (Wilson). Under side—margins near Saffron Yellow, Plate 7/1, page 7 (Wilson), with remainder near Aureolin, Plate 3/3, page 3 (Wilson).

Pollen: Moderate to abundant.

*Color.*—Near Indian Yellow, Plate 6, page 6 (Wilson).

Pistils: Many; approximately 125 in number.

Styles: Moderately even; average length; from 6 to 10 mm. in length– average caliper; bunched.

*Color.*—Near Sap Green, Plate 62/3, page 62 (Wilson), with upper ¼ overlaid with near Carmine, Plate 21/2, page 21 (Wilson).

Stigma:

*Color.*—Between Primrose Yellow, Plate 601/2, page 65 (Wilson) and Empire Yellow, Plate 603/2, page 66 (Wilson).

Ovaries: Most enclosed in calyx, but some protruding therefrom.

Hips: None.

Sepals: Permanent; medium length; recurved.

*Color.*—Inside—Between Biscay Green, Plate XVII (Ridgway) and Bice Green, Plate XVII (Ridgway); masked by white woolly tomentum. Outside—between Biscay Green, Plate XVII (Ridgway) and Bice Green, Plate XVII (Ridgway); sometimes overlaid with near Deep Corinthian Red, Plate XXVII (Ridgway).

Seeds: None.

PLANT

Foliage:

*Leaves.*—Compound of usually 5 to 7 leaflets; abundant; medium size; moderately heavy; leathery; semi-glossy.

*Leaflets.*—Shape—ovoid, with apex acute. Base—round. Margin—simply serrate.

*Color.*—Mature: Upper surface—near Dark Dull Yellow-Green, Plate XXXII (Ridgway); under surface—near Chromium Green, Plate XXXII (Ridgway). Young: Upper surface—between Biscay Green, Plate XVII (Ridgway) and Bice Green, Plate XVII (Ridgway), overlaid with near Neutral Red, Plate XXXVIII (Ridgway) particularly along margins; Under surface—near Courge Green, Plate XVII (Ridgway), overlaid heavily with near Corinthian Purple, Plate XXXVIII (Ridgway).

*Rachis (the supporting stem of the compound leaf).*—Average size.

Upper side—grooved; hairy; many stipitate glands on edges.

Under side—moderately prickly; with few stipitate glands.

*Stipules.*—Medium length; medium width; with medium length points turning out at an angle of more than 45°.

*Disease resistance.*—Average resistance to mildew as compared with other varieties grown under comparable cultural conditions at Ontario, California.

Growth:

*Habit.*—Bushy; upright, but somewhat spreading; much-branched.

*Growth.*—Vigorous.

*Canes.*—Medium caliper to heavy.

*Main stems.*—Color—between Oil Green, Plate V (Ridgway) and Spinach Green, Plate V (Ridgway). Large prickles—several to many; medium length; almost straight; with moderately short, round base. Color—near Light Drab, Plate XLVI (Ridgway). Small prickles—several. Color—between Light Drab, Plate XLVI (Ridgway) and Cinnamon Drab, Plate XLVI (Ridgway). Hairs—none.

*Branches.*—Color—near Bice Green, Plate XVII (Ridgway). Large prickles—several to many; medium length; almost straight; with moderately short, round base. Color—near Tawny-Olive, Plate XXIX (Ridgway). Small prickles—several. Color—near Tawny-Olive, Plate XXIX (Ridgway). Hairs—none.

*New shoots.*—Color—between Biscay Green, Plate XVII (Ridgway) and Light Elm Green, Plate XVII (Ridgway), overlaid heavily with near Neutral Red, Plate XXXVIII (Ridgway). Large prickles—several; medium length; almost straight; with moderately short, round base. Color—between Corinthian Purple, Plate XXXVIII (Ridgway) and Neutral Red, Plate XXXVIII (Ridgway). Small prickles—several. Color—near Corinthian Purple, Plate XXXVIII (Ridgway). Hairs—none.

I claim:

A new and distinct variety of rose plant of the hybrid polyantha class, substantially as herein shown and described, characterized particularly as to novelty by the relatively large size of its double blooms, the cluster blooming habit thereof, the light yellow general color tonality of its blooms, and its abundant foliage which covers the plant well.

No references cited.